United States Patent [19]

Tan et al.

[11] Patent Number: 4,916,235

[45] Date of Patent: Apr. 10, 1990

[54] RESIN SYSTEMS DERIVED FROM BENZOCYCLOBUTENE-MALEIMIDE COMPOUNDS

[75] Inventors: Loon-Seng Tan; Fred E. Arnold, both of Centerville, Ohio

[73] Assignee: University of Dayton, Dayton, Ohio

[21] Appl. No.: 935,447

[22] Filed: Nov. 26, 1986

[51] Int. Cl.$^4$ ............................................. C07D 209/48
[52] U.S. Cl. ................................. 548/461; 548/465; 548/466; 548/547; 548/549
[58] Field of Search ............... 548/549, 466, 461, 465, 548/547

[56] References Cited

U.S. PATENT DOCUMENTS

| | | | |
|---|---|---|---|
| 4,540,763 | 9/1985 | Kirchhoff | 526/281 |
| 4,570,011 | 2/1986 | So | 560/8 |
| 4,661,193 | 4/1987 | Kirchhoff et al. | 156/334 |
| 4,724,260 | 2/1988 | Kirchhoff et al. | 526/258 |
| 4,731,418 | 3/1988 | Dean | 525/203 |

FOREIGN PATENT DOCUMENTS 8610072 10/1986 European Pat. Off. .

OTHER PUBLICATIONS

L. Tan et al., Chem. Abstracts, vol. 105: 209412s (1986).

*Primary Examiner*—Mary E. Ceperley
*Attorney, Agent, or Firm*—Biebel, French & Nauman

[57] ABSTRACT

Resins are prepared by Diels-Alder polymerization of compounds of the formula

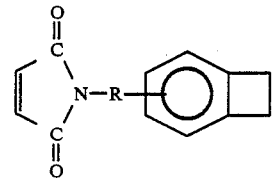

(I)

where R is a divalent linking group.

7 Claims, 2 Drawing Sheets

RESIN SYSTEMS DERIVED FROM BENZOCYCLOBUTENE-MALEIMIDE COMPOUNDS

The U.S. Government has rights in this invention pursuant to Contract No. F33615-84-C-5020 awarded by the Department of the Air Force.

BACKGROUND OF THE INVENTION

The present invention relates to resins obtained by Diels-Alder polymerization, and more particularly, to high temperature resistant matrix resins obtained by Diels-Alder polymerization of benzocyclobutene-maleimide compounds.

The Diels-Alder reaction is a cycloaddition reaction in which an unsaturated group, which is a dienophile, combines with a 1,3-diene to form a six membered ring. The Diels-Alder reaction appears to be favored by the presence of the diene's electron-yielding groups, and the dienophile's electron-attracting groups.

Although the Diels-Alder reaction is used extensively in organic chemistry, it is less commonly employed in polymer chemistry. Yet, it can be quite advantageous. For example, at high temperatures, it is expected that Diels-Alder adducts with appropriate activating groups (unsaturated and conjugated groups) undergo conversion to other products, such as aromatic rings, before the temperature required for the reverse reaction or degradation process is reached; consequently, such Diels-Alder polymers exhibit high thermal stability.

In most Diels-Alder polymerizations, a bis-diene reacts with a bis-dienophile. For example, in W. J. Bailey et al, "Polymeric Diels-Alder Reactions," *J. Org. Chem.* 27, 3295(1962), 2-vinylbutadiene, a bi-functional diene, is reacted with benzoquinone, a dienophile. J. K. Stille, "Cycloaddition Polymerization," *Die Makromolekulare Chemie* 154, 49(1972), teaches that cyclopentadienones undergo a variety of Diels-Alder reactions depending on the ring substitution, dienophile, and reaction conditions. To obtain a monoadduct, cyclopentadienone is employed with an acetylenic dienophile to obtain an aromatic product. Additionally, R. T. Kohl et al, "Diels-Alder Reactions of Phenyl-Substituted 2-Pyrones: Direction of Addition with Phenylacetylene," *Macromolecules* 11, 340(1978) shows the Diels-Alder reactions of substituted acetylenes with 2-pyrones. J. N. Braham et al, "Polyphenylenes via Bis(2-pyrones) and Diethynylbenzenes, "The Effect of m- and p-Phenylene Units in the Chain," *Macromolecules* 11,343(1978) shows the Diels-Alder 4+2 cycloaddition reaction of bis(2-pyrone) monomers with diethynylbenzenes.

In some Diels-Alder polymerizations, the same molecule contains both the diene and the dienophile moiety. One class of monomer is capable of functioning as both a diene and dienophile. Cyclopentadiene and 2-vinylbutadiene are two examples. In another class of monomer, the diene and dienophile are different. Meek and Argabright, *J. Org. Chem.* 22, 1708(1957) prepared 6-[p-(p-maleimidobenzoyloxy)phenyl]-1,2,3,4-tetrachlorofulvene which contains a maleimido group as a dienophile and a perchlorofulvene group as a diene. W. J. Bailey, "Diels-Alder Polymerization, " *Step-Growth Polymerization*, Marcel Dekker, New York, 1972, stresses that this type of polymerization presents considerable difficulty.

Benzocyclobutene functions very well in a Diels-Alder reaction. As taught by W. Oppolzer, *Synthesis* 793(1978), under appropriate thermal conditions, the benzocyclobutene unit undergoes an electrocyclic ring opening to form the more reactive o-xylylene functionality. O-xylylene is a powerful diene and, engages in a Diels-Alder reaction in the presence of a suitable dienophile. See Boekelheide, *Accounts Chem. Res.* 13, 65(1980).

An example of a suitable dienophile is a maleimide. Maleimides are well-known as possessing strong dienophilicity. The dienophilic site, i.e., the carbon-carbon double bond, is not subjected to the substituent effect imposed by the rest of the structure. Thus, a maleimide engages in a Diels-Alder polymerization in the presence of a suitable diene such as o-xylylene.

Bis-benzocyclobutenes and polymers derived therefrom are disclosed in U.S. Pat. No. 4,540,763. The bis-benzocyclobutenes are connected by direct bond or a bridging member such as a cyclic imido group. In general, the polymers are obtained by addition polymerization wherein the fused cyclobutene rings undergo thermal transformation to o-xylylene moieties which can react with one another.

SUMMARY OF THE INVENTION

An object of the present invention is to provide compounds which are polymerizable by Diels-Alder polymerization.

Another object of the present invention is to provide compounds useful in the preparation of high-temperature resistant matrix resins by Diels-Alder polymerization.

A more particular object of the present invention is to provide high-temperature resistant matrix resins prepared by Diels-Alder polymerization of benzocyclobutene-maleimide compounds.

Another object of the present invention is to provide high-temperature resistant matrix resins which are useful in composite materials in the advanced aircraft and aerospace vehicles.

A further object of the present invention is to provide high-temperature resistant matrix resins which can be aromatized at high temperature.

In accordance with the present invention, resins are obtained by the Diels-Alder polymerization of compounds which exhibit both diene and dienophile functionalities. The present invention provides compounds of the general formula (I)

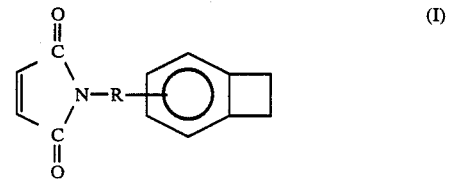

wherein R is a divalent linking group. Upon heating these compounds to about 200° C., the benzocyclobutene unit undergoes an electrocyclic ring-opening to form the more reactive o-xylylene functionality which engages in a Diels-Alder polymerization with the maleimide unit of the compound to form a six membered ring which conceivably can be converted to highly thermally stable structures such as a benzene ring and/or benzoquinone structure, at high temperatures.

The maleimide functionality is ideal as the dienophilic component for a Diels-Alder polymerization and offers several advantages over other dienophilic components. The starting material for maleimide, i.e., maleic anhydride, is fairly inexpensive compared to starting materials required for other dienophilic components. The preparation of maleimide does not involve the use of an expensive catalyst. Also, the dienophilicity of maleimide is known to greatly exceed that of other dienophiles.

In a more particular embodiment, the compound is represented by the formula (II)

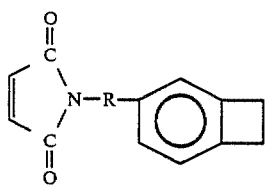
(II)

where R is a divalent linking group.

To maximize the thermal stability of the resin, in the compound of formulas (I) and (II) above, R is selected so as to provide a linking group which is as thermooxidatively stable as the Diels-Alder polymerization bond. Thus, in a preferred embodiment, R is an aromatic divalent linking group, and more particularly, a benzimido group. In other applications where thermooxidative stability is not as critical, numerous R groups are useful in the compounds of the present invention.

In one embodiment, R is a direct bond.

In another embodiment, R is represented by the formula (IV)

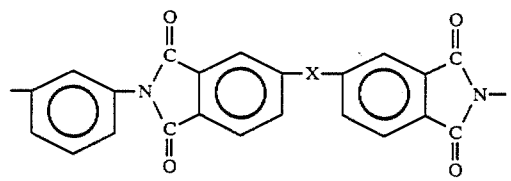
(IV)

where X is a divalent linking group.

In a more particular embodiment, X is selected from the group consisting of —C(CF$_3$)$_2$—, —C(CH$_3$)$_2$—, —CH$_2$—, —O—, —S—, —CO—, —SO$_2$—, and a direct bond.

In another embodiment, X is represented by the formula (V)

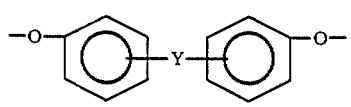
(V)

where Y is selected from the group consisting of —C(CF$_3$)$_2$—, —C(CH$_3$)$_2$—, —CH$_2$—, —O—, —S—, —CO—, —SO$_2$— and a direct bond.

In an additional embodiment, X is represented by the formula (VI)

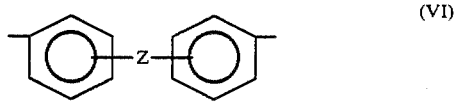
(VI)

where Z is selected from the group consisting of —C(CF$_3$)$_2$—, —C(CH$_3$)$_2$—, —CH$_2$—, —O—, —S—, —CO—, —SO$_2$— and a direct bond.

In another embodiment, R is represented by the formula (vII)

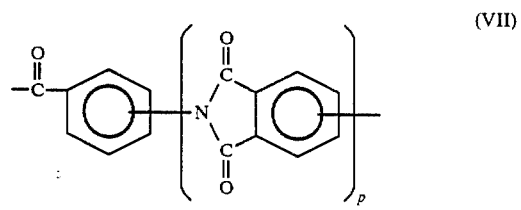
(VII)

where p is 0 or 1.

In a preferred embodiment, R is represented by the formula (III)

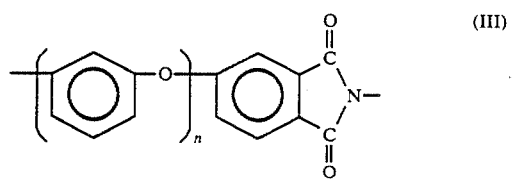
(III)

where n is 0 or 1. In a particularly preferred embodiment, n is 0.

Some resins with excellent high temperature stability are obtained by Diels-Alder polymerization of compounds of the formula (I) above where R is represented by the formula (III) above.

Other objects and advantages of the invention will be apparent from the following description, the accompanying drawings and the appended claims.

DETAILED DESCRIPTION OF THE INVENTION

Figure 1:
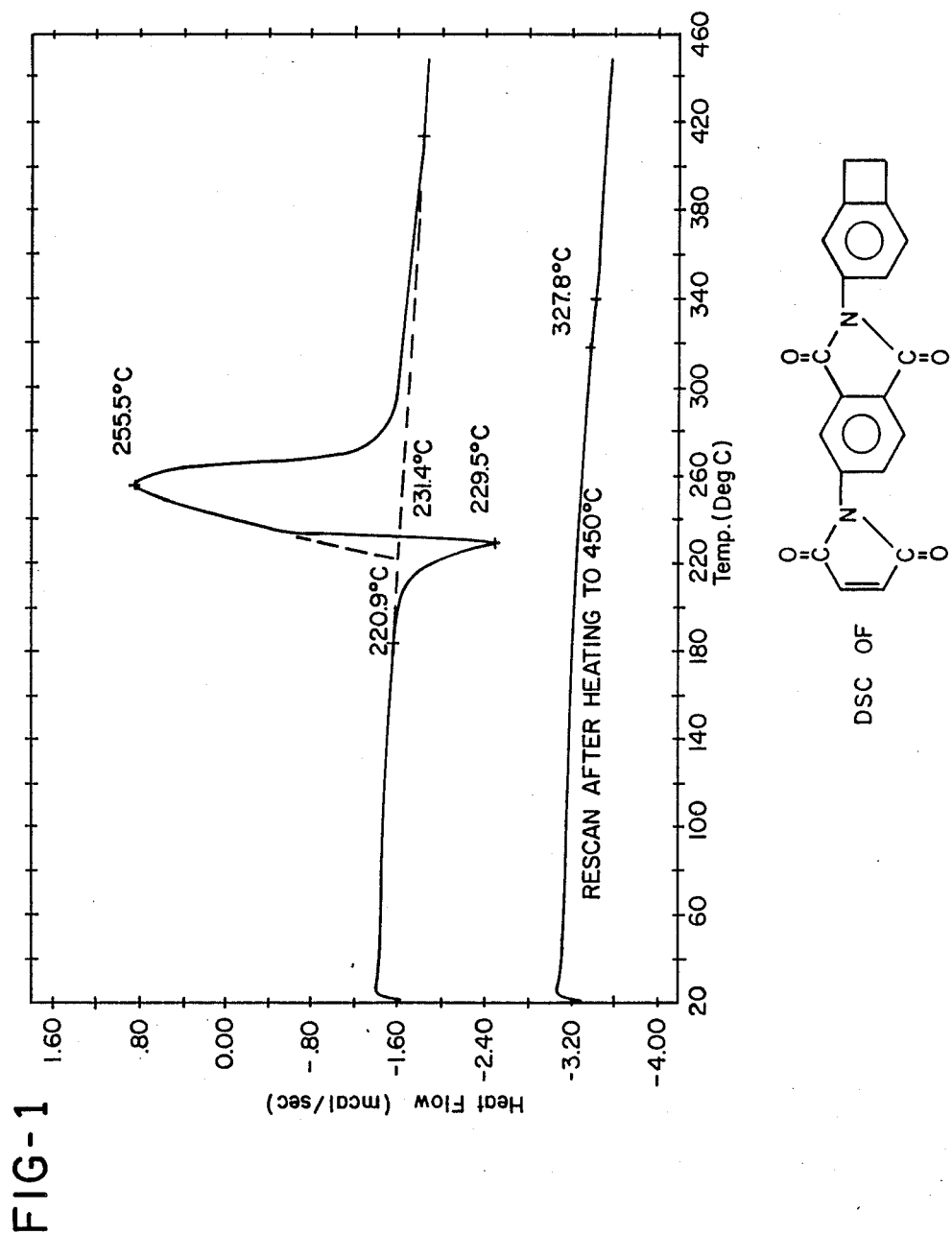
FIG. 1 is a Differential Scanning Calorimetric (DSC) curve of N-(4-benzocyclobutenyl)-4(N-maleimido)-phthalimide.

The following reaction scheme sets forth the synthesis of 4-aminobenzocyclobutene.

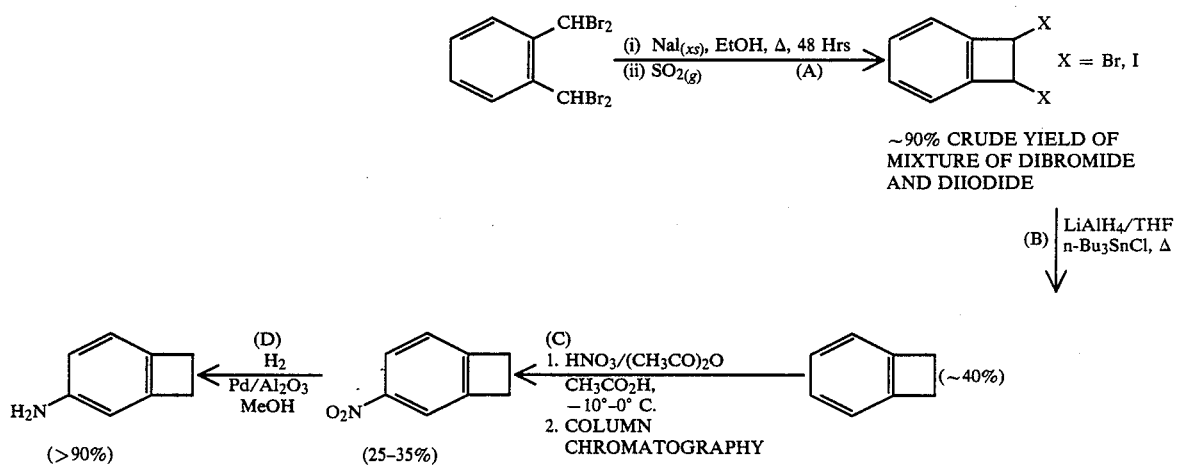

~90% CRUDE YIELD OF
MIXTURE OF DIBROMIDE
AND DIIODIDE

Step (A) is explained in Cava and Napier, *J. Am. Chem. Soc.* 79, 1701 (1957). Sanders and Giering, *J. Org. Chem.* 38, 3055 (1973) provides details on Step (B). Step (C) is discussed in Lloyd and Ongley, *Tetrahedron* 20, 2185 (1964) while Step (D) is discussed in Horner and Schmelzer, *Chem Ber* 93 1774 (1960).

To prepare a compound of the formula (II) where R is a direct bond, 4-aminobenzocyclobutene is reacted with freshly purified maleic anhydride in methylene chloride at room temperature to lead to the formation of yellow maleamic acid. Subsequent treatment of N-4-benzocyclobutenyl maleamic acid with the dehydrating agent, acetic anhydride and in the presence of triethylamine and nickel acetate tetrahydrate provides the desired maleimide.

To prepare a compound of the formula (II) wherein R is represented by the formula (III) where n is 0, 4-aminobenzocyclobutene and commercially available 4-nitrophthalic anhydride are condensed in a mixed solvent of acetic acid and toluene under Dean-Stark conditions. The resulting product is subsequently subjected to catalytic hydrogenation in the presence of 10% palladium on carbon and anhydrous magnesium sulfate and using ethyl acetate as solvent. Finally, the desired compound is prepared from the foregoing amine and maleic anhydride in $CH_2Cl_2$/ethyl acetate followed by cyclodehydration of the maleamic acid intermediate using the established reagents and solvent (acetic anhydride, triethylamine, nickel acetate tetrahydrate and acetone).

To prepare a compound of the formula (II) wherein R is represented by the formula (IV) and X is $-C(CF_3)_2-$, a heterogeneous mixture of 2,2'-bis(phthalimido)-hexafluoropropane and 3-nitroaniline is stirred in toluene under a nitrogen atmosphere at room temperature for four days. The stoichiometry of the dianhydride and the amine is 1:1.1 and the reaction is monitored by thin-layer chromatography. The mono-amic acid with some contamination of the diamic acid and the starting dianhydride is collected by filtration. It is then heated in a large beaker in an oven set at 170°–175° C. for one hour. The solid is then dissolved in minimal amount of methylene chloride. The resulting solution is then purified by column chromatography. The isolated imide-anhydride, 2-(4-phthalic anhydrido)-2'-(4-N-3-nitrophenyl phthalic imido) hexafluoropropane is then treated with 4-aminobenzocyclobutene in dimethyl acetamide at room temperature followed by dehydrating agents, acetic anhydride/pyridine. The asymmetric diimide, 2-(N-4-benzocyclobutenyl phthalimido)-2'-(4-N-3-nitrophenyl phthalic imido)hexafluoropropane is subsequently catalytically hydrogenated using 10% palladium on carbon, a mixed solvent of ethyl acetate and methanol and ammonium formate as a hydrogen source. The isolated amine, 2-(N-4-benzocyclobutenyl phthalic imido)-2'-(4-N-3-aminophenyl phthalic imido)hexafluoropropane is reacted with maleic anhydride to form the intermediate maleamic acid which upon cyclodehydration using established reagents and solvent yields the desired maleimide, 2-(N-4-benzocyclobutenyl phthalic imido)-2'-[4-N-(3-maleimido-phenyl) phthalic imido] hexafluoropropane.

To prepare a compound of the formula (II) wherein R is represented by the formula (VII) where p is 0 and the isomer is meta, Friedel-Crafts reaction of benzocyclobutene and 3-nitrobenzoyl chloride in methylene chloride using antimony pentachloride as the catalyst and at low temperature leads to the formation of 4-benzocyclobutenyl-3-aminophenyl ketone. Catalytic transfer hydrogenation of the foregoing nitro-compound in methanol using 10% palladium on carbon and ammonium formate as the source of hydrogen atoms is the next step. The desired maleimide is prepared by the reaction of 4-benzocyclobutenyl-3-aminophenyl ketone with maleic anhydride under established conditions.

The para-isomer is prepared via the same synthetic route.

To prepare a compound of the formula (II) wherein R is represented by the formula (VII) where p is 1, the initial amic acid is prepared from 4-nitrophthalic anhydride and 3-aminophenyl-4-benzocyclobutenyl ketone in dimethyl acetamide at room temperature under nitrogen. The cyclodehydration of the amic acid leads to the corresponding imide using acetic anhydride and pyridine. Catalytic transfer hydrogenation of the foregoing nitro-compound using 10% palladium on carbon, methanol and ethyl acetate as co-solvents and ammonium formate as the hydrogen source results in the isolation of the corresponding amine. Reaction with maleic anhydride under established conditions affords the desired maleimide.

The preferred methods of preparation of certain benzocyclobutene-maleimide compounds useful in the present invention are described in the Examples below.

In general, the resins of the present invention are prepared by Diels-Alder polymerization of the particular compounds used. Upon heating the compounds to about 200° C., Diels-Alder polymerization occurs. Also, homopolymerization of both the maleimide and the benzocyclobutene functionality can occur simultaneously with the Diels-Alder polymerization. These potential polymerization reactions are set forth in the following scheme.

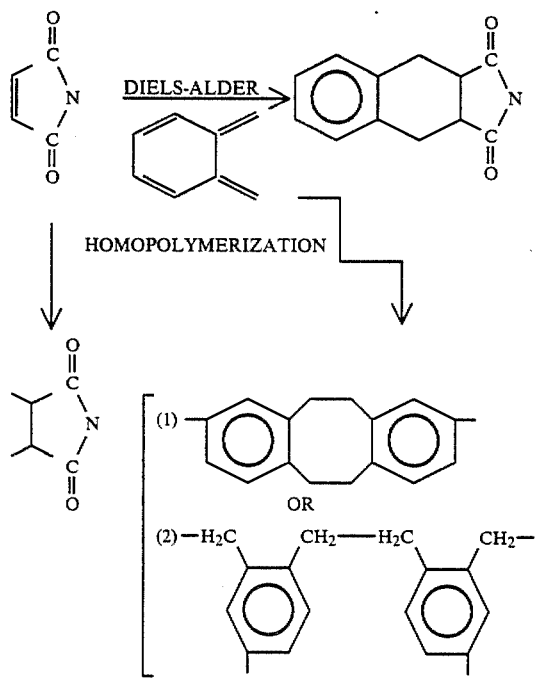

In the Diels-Alder polymerization, the benzocyclobutene undergoes an electrocyclic ring-opening to form the more reactive o-xylylene functionality wherein the o-xylylene functionality undergoes cycloaddition with a maleimide functionaliry. In the homopolymerization of the maleimide, the maleimide functionality undergoes cycloaddition with another maleimide functionality. In the homopolymerization of benzocyclobutene, the benzocyclobutene reacts with another benzocyclobutene by one of at least two possible pathways: (1) cycloaddition and (2) linear addition. (1) Following the cycloaddition mode, a polymer with an eight membered ring is believed to form. (2) Following the linear addition mode, a polymeric structure with a double strand of poly (o-xylylene) connected by aromatic bridging groups is believed to result. The terms "cycloaddition" and "linear addition" are used to describe the structures and do not implicate the mechanisms from which they arise.

In preparing the resins of the present invention, the Diels-Alder polymerization occurs at a substantially greater rate than the homopolymerization of the maleimide or the benzocyclobutene functionality in order to maximize the thermal stability of the resins. Thus, the resulting product has minimal homopolymerization product and maximum Diels-Alder polymerization product. In general, Diels-Alder polymerization occurs at a temperature of about 200°–250° C. while homopolymerization occurs at a temperature of about 185°–240° C.

An example of a Diels-Alder polymerization scheme is set forth below for N-(4-benzocyclobutenyl)-4(N-maleimido)phthalimide.

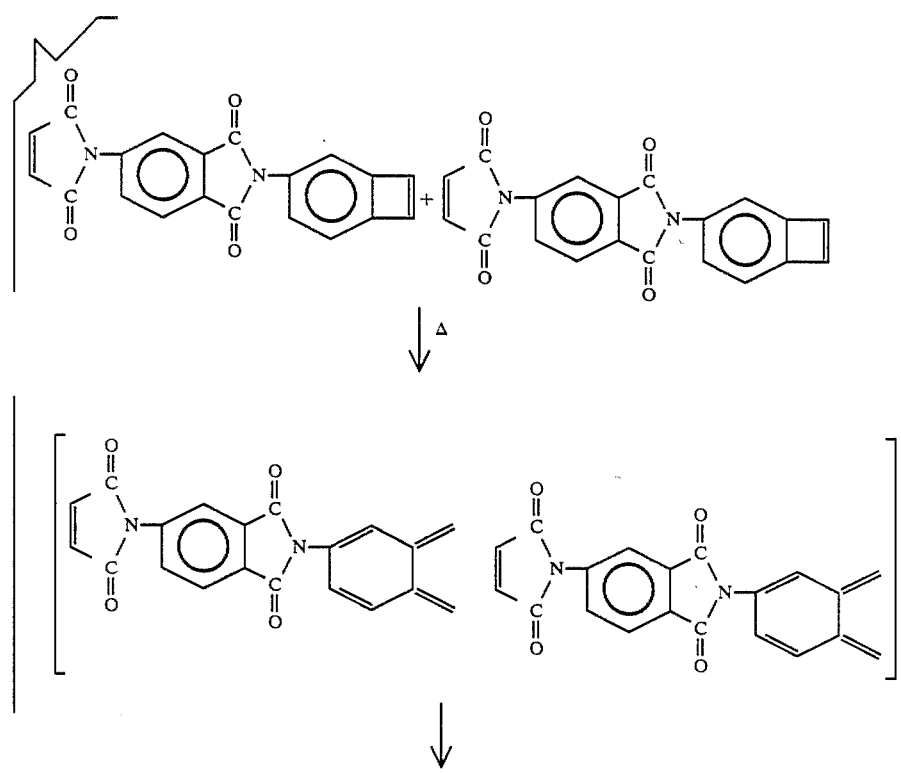

-continued

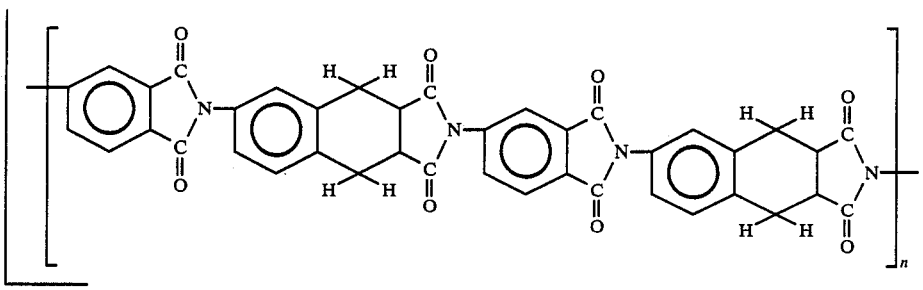

A Differential Scanning Calorimetric (DSC) study indicates the endothermic or exothermic nature of a reaction as the temperature increases. Typically, the reaction temperature is plotted on the abscissa while the heat flow is plotted on the ordinate. The DSC study is useful in the present invention because it indicates the exotherms for a given compound. For example, when R is represented by formula (III) where n equals 0 in the compound of formula (II) above, the DSC is represented by FIG. 1. FIG. 1 shows a $T_{poly\ onset}$ (beginning polymerization temperature) of about 221° C. The $T_m$ (melting temperature) is about 230° C. FIG. 1 shows a $T_{poly\ max}$ (temperature at which polymerization reaches its maximum) of about 256° C. Rescanning the sample after heating to 450° C. shows a $T_{g(cure)}$ (glass transition temperature of the polymer) of about 328° C.

The $T_{poly}$ and $T_m$ valves were obtained by subjecting a compound sample to DSC measurements, which indicate the amounts of heat absorbed (endothermic) or evolved (exothermic) with respect to a reference temperature point or range when the sample undergoes either chemical chnges ($T_{poly}$) or physical changes ($T_m$). $T_{g(cure)}$ was determined both by DSC and thermomechanical analyses which employ a sensitive probe to detect the softening point of the sample at its surface.

Table 1 sets forth thermal characteristics of compounds of formula (II).

TABLE 1

THERMAL CHARACTERISTICS OF COMPOUNDS OF FORMULA (II)

| Example | Tg(ini) | Tm | T poly Onset | T poly Max | Tg(cure) | Tdec | T10% |
|---|---|---|---|---|---|---|---|
| 5 | −20° | 77° | 228°[a] | 259°[a] | 287° | —[b] | —[b] |
| 8(meta) | 3° | 93° | 224° | 261° | 249° | 431° | 470° |
| 8(para) | — | — | 188° | 248° | — | 353° | 400° |
| 3 | 86° | 230° | 231° | 256° | 328° | 484° | 498° |
| 11 | 44° | — | 198° | 257° | 258° | 403° | 452° |

All Table 1 temperatures are expressed in °C. Example numbers correspond to the Examples given below. $T_g$(ini) is the initial glass transition temperature and was determined from the rescan of a sample previously heated just past the melting temperature, $T_m$. Tpoly onset is the beginning polymerization temperature while Tpoly max is the temperature at which polymerization reaches its maximum. $T_g$(cure) is the final glass transition temperature and was determined from the rescan of the sample previously heated to 450° C. $T_{dec}$ is the temperature at which major decomposition or weight loss occurs as observed by TGA. Both TGA and DSC runs were conducted at 10° C./min. TGA was run under air and DSC was run under $N_2$. $T_{10\%}$ is the temperature at which 10% of the original weight of the sample is lost during the TGA run. Values a were determined under a $N_2$ pressure of 500 psi. For values b, when a sample was run under atmospheric pressure, volatilization of the compound began at 148° C.; about 71% of the original weight was lost between 200°-238° C.

Figure 2:
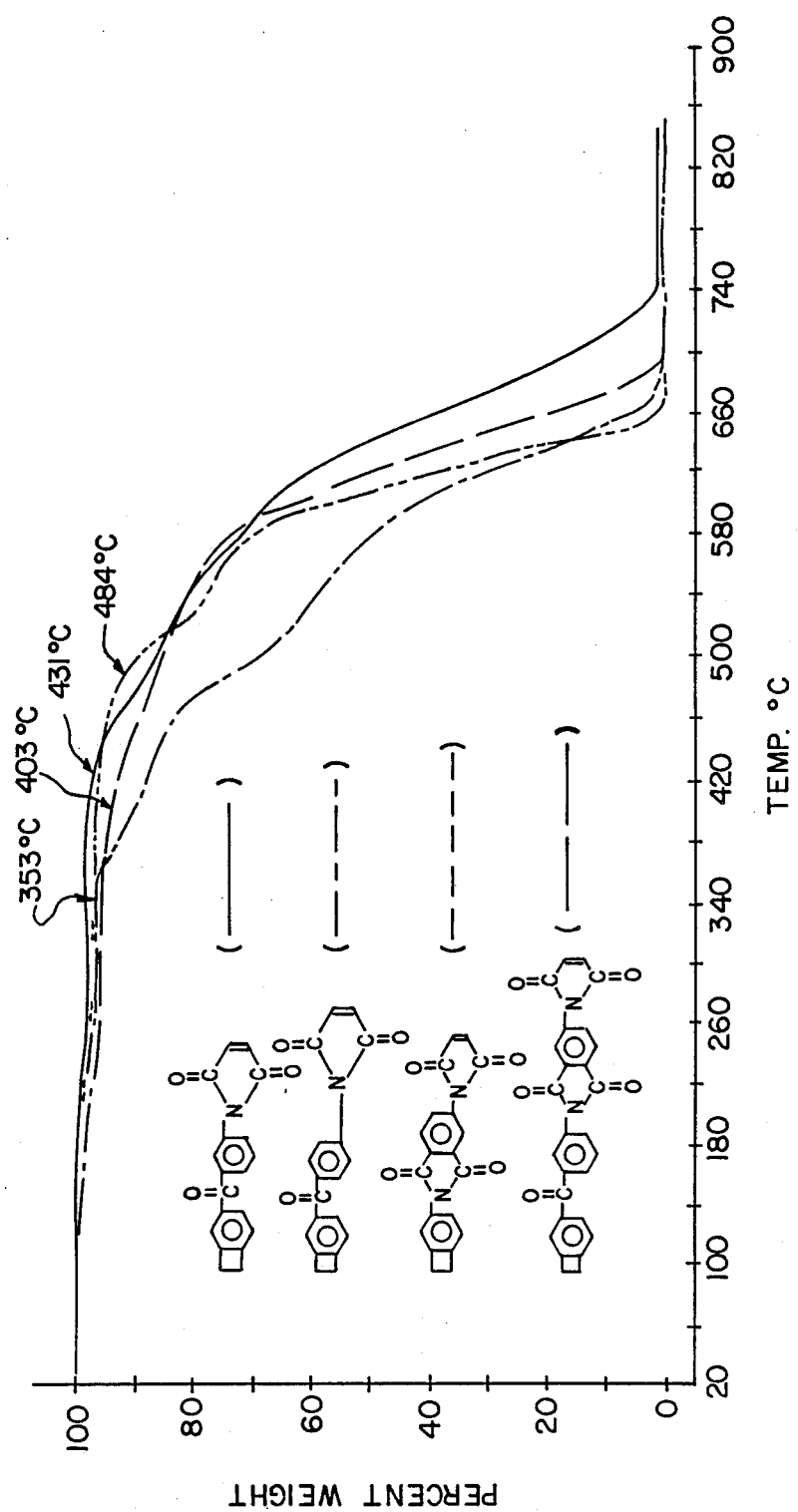
FIG. 2 is a Composite Thermogram of the Thermogravimetric Analysis (TGA) of compounds of formula (II).

FIG. 2 represents a composite thermogram of the thermogravimetic analysis (TGA) of compounds of formula (II). The extrapolated values at which the major decompositions began ($T_{dec}$) are indicated.

It is believed that the resultant resin can be aromatized at high-temperature in the presence of air ($O_2$) to enhance the thermodynamic stability of the final polymeric structure. Although gaseous $H_2O$ will be produced as volatiles in the aromatization process, such process will take place primarily on the surface of the thermosets and will have minimal formation of voids.

The Diels-Alder polymerization of the compounds has a significant impact on the nature and properties of the resins prepared. In a particularly preferred embodiment, resins prepared by the Diels-Alder polymerization of compounds of the formula (II) above where R is represented by formula (III) where n is 0 are high temperature resistant matrix resins useful in composite materials in the advanced aircraft and aerospace vehicles.

The present invention is illustrated in more detail by the following non-limiting examples.

EXAMPLE 1

Preparation of N-4-Benzocyclobutenyl 4-nitro phthalimide.

A mixture of 4-nitro phthalic anhydride (3.57 g, 18.5 mmol) and freshly prepared 4-aminobenzocyclobutene 2.20 g (18.5 mmol) was heated to reflux in acetic acid (100 ml) and toluene (100 ml) under nitrogen. The water of condensation was removed continuously and azeotropically using a Dean-Stark trap. After about 17 hrs, the dark but homogeneous reaction mixture was allowed to cool to room temperature and poured into 600 ml water. The mixture was then extracted with ethyl acetate (100 ml, then 4 ×50 ml). The organic extract was washed with aq. $NaHCO_3$ and then $H_2O$, and finally dried over $MgSO_4$. Immediately after the removal of hydrated $MgSO_4$ by filtration, the filtrate was subjected to rotary evaporation to provide slightly tacky yellow-green crude product, which was redissolved in $CH_2Cl_2$. The resultant solution was filtered through a bed of silica gel (approximately 20 g) and washed with $CH_2Cl_2$ until the filtrate was colorless. The combined filtrate was again stripped on a rotary evaporator to afford yellow plates, which was collected on a fitted filter funnel, washed with petroleum ether and dried in oven under vacuum at 80° C. overnight. Yield 3.85 g (71%). Calc. for $C_{16}H_{10}N_2O_4$:65.30% C; 3.42% H;

9.52% N. Found: 64.17% C; 3.29% H; 9.54% N. Mass Spectroscopy: M+(294, 100%).

EXAMPLE 2

Preparation of N-4-Benzocyclobutenyl-4-aminophthalimide.

1.50 g (5.10 mmol) of N-4 benzocyclobutenyl-4-nitrophthalimide, 1.70 g of MgSO$_4$, 0.2 g of 10% Pd/C and 60 ml of ethyl acetate were placed in a pressure bottle and the mixture was then rocked on a hydrogenator under initial hydrogen pressure of 60 psi for about 17 hrs. The resultant reaction mixture, which was yellow-green, was filtered through celite and the solid residue was washed with acetone until the filtrate was colorless. The combined yellow-green filtrate was stripped to dryness to provide greenish yellow product, which was collected on a fritted filter funnel, washed with petroleum ether and dried in vacuo overnight. Yield: 1.20 g (88.9%). The product was used in the subsequent reaction without further purification. Mass Spectroscopy: M+(264 100%). IR (KBr plate): $\nu$(NH$_2$):3290 m, 3390 m cm$^{-1}$; $\nu$(CH$_2$) 2860 w, 2940 m; $\nu$(imide): 1773 ms, 1690 vs cm$^{-1}$, $\delta$(imide) 744 ms, $^1$HNMR (acetone): 2.93 ppm (s, broad 2H); 3.23 ppm (5.4 H): 7.45 (center, complex, 6 H).

EXAMPLE 3

Preparation of N-(4-benzocyclobutenyl)-4(N-maleimido) phthalimide.

1.60 g (6.05 mmol) of N-(4-benzocyclobutenyl)-4-amino phthalimide and 0.60 g (6.08 mmol) of maleic anhydride were placed in a 250 ml round-bottomed flask. 150 ml of CH$_2$Cl$_2$ was added and the resultant suspension was heated to reflux. After 2 hrs, there was no indication that the amine was dissolving in refluxing CH$_2$Cl$_2$. Therefore, about 40 ml of ethyl acetate was added to dissolve some of the amine and the reaction mixture was refluxed overnight. The following morning found the reaction mixture was containing a lot of light yellow precipitates. Hence, it was allowed to cool to r.t. and solvent was removed completely by rotary evaporation. To the resultant maleic amic acid was added 200 ml acetone, 0.25 g Ni(OAc)$_2$·4H$_2$O, and a solution of 1 ml NEt$_3$ and 2 ml of acetic anhydride when NEt$_3$/Ac$_2$O was added, the reaction mixture turned completely clear (but still yellow). It was heated to gentle reflux and maintained at reflux for 6 hrs. After the reaction mixture had been allowed to cool to r.t., it was stripped completely to afford light yellow solid as crude product. Dissolving the crude product in CH$_2$Cl$_2$, treating the resultant solution with solid NaHCO$_3$ and finally filtering it through a bed of silica gel, bright yellow powder was obtained after removal of the solvent from the filtrate by rotary evaporation. Yield: 1.85 g (88.9%). (The product was soluble in CH$_2$Cl$_2$ but insoluble in CHCl$_3$ and acetone). Calc. for C$_{20}$H$_{12}$O$_4$N$_2$: 69.76% C; 3.51% H; 8.14% N. Found: 68.05% C; 3.50% H; 8.50% N. Mass Spectroscopy: M+(344, 100%). IR (KBr): $\nu$(alicyclic CH$_2$) 2975 w, 2962 w, 2934 m; $\nu$(aromatic imide) 1772 m, 1715 vs; $\delta$(aromatic imide): 705 m.

EXAMPLE 4

Preparation of N-phenyl-maleamic acid.

2.80 g (28.55 mmole) of maleic anhydride was dissolved completely in about 60 ml of methylene chloride. To this solution was added the freshly prepared 4-aminobenzocyclobutene (3.35 g., 28.11 mmole). Immediately, bright yellow precipitates formed quantitatively. The reaction was quite exothermic as evidenced by the self-refluxing of methylene chloride. Additional 30 ml of methylene chloride was added to moderate the reaction temperature. Finally, the resultant bright yellow heterogeneous mixture was stirred overnight at room temperature. The reaction mixture was filtered and the yellow solid product collected was washed with methylene chloride (3 ×25 ml) and air-dried. Yield: 5.03 g (82.4%). Anal Calc. for C$_{12}$H$_{11}$NO$_3$: C, 66.35; H, 5.10; N, 6.45. Found: C, 66.66; H, 5.27; N, 6.34.

EXAMPLE 5

Preparation of N-4-benzocyclobutenyl maleimide.

N-phenyl-maleamic acid (6.00 g, 27.62 mmol) was partially dissolved in about 100 ml of acetone in a 250 ml round-bottomed flask. To this stirred heterogeneous mixture was added solid nickel acetate tetrahydrate (0.25 g), followed by the mixture of acetic anhydride (6.27 g. 61.42 mmol) and triethylamine (1.82 g, 23.0 mmol). Gradually, almost all the solids dissolved and the resultant reaction mixture was stirred at room temperature for two days. After all the solvent had been removed by rotary evaporation, the residual oil (smell of acetic acid) was mixed with a small amount of methylene chloride. The solution was passed through a small column containing silica gel saturated with hexane. The column was eluted with hexane until the yellow band developed reached its bottom. Then, it was eluted with methylene chloride. The second yellow fraction collected was then subjected to rotary evaporation and hexane was then added slowly to the concentrated solution to precipitate the product as a yellow solid. The product was collected, washed with hexane and air-dried overnight. Yield: 4.34 g (78.9%). Anal Calc. for C$_{12}$H$_9$NO$_2$: C, 72.35; H, 4.55; N, 7.03. Found: C, 71.84; H, 4.54; N, 6.90. Mass Spectroscopy: M+, 199 (100%). Proton NMR (CDCl$_3$),$\delta$(ppm): 3.23 (singlet, 4H, alicyclic protons); 6.87 (singlet, 2H, olefinic protons); 7.03-7.33 (complex, 3H, aromatic protons). IR (KBr): $\nu$(maleimide): 1710 cm$^{-1}$, vs; 1772 cm$^{-1}$, W.

EXAMPLE 6

Preparation of 4-benzocyclobutenyl-3-nitrophenyl ketone.

8.91 g (48.0 mmol) of 3-nitrobenzoyl chloride was placed in a 500 ml 3 necked round-bottomed flask equipped with a mechanical stirrer, a thermometer and an addition funnel capped with a nitrogen inlet-adaptor. About 200 ml of methylene chloride was added and the resultant colorless solution was subsequently chilled to about −15° C. under nitrogen. A methylene chloride (20 ml) solution of antimony pentachloride (11.05 g, 48.25 mmol) was then added dropwise over a period of 20 minutes. The yellow and homogeneous reaction mixture was allowed to warm up to about 0° C., at which temperature it was continuously stirred for another 30 minutes. Then, it was chilled again to about −20° C. and a methylene chloride (30 ml) solution of benzocyclobutene (5.00 g, 48.0 mmol) was delivered via the addition funnel over a period of about 15 minutes. The reaction mixture slowly became dark and then bright yellow precipitates formed. At the end of the addition, the yellow reaction mixture was stirred at −20° C. for another hour and then allowed to warm up to room temperature on its own. Upon reaching room temperature, the reaction mixture was green and heterogeneous. It was stirred at room temperature overnight. The green reaction mixture was poured into a 2-liter beaker containing about 1000 g of ice cubes. The mixture was then stirred vigorously until all the ice melted. Two layers appeared; the methylene chloride layer was dark green and the aqueous layer was white and opaque. The methylene chloride solution was separated from the aqueous layer via a separatory funnel. The aqueous phase was subsequently extracted with two portions (30 ml) of methylene chloride. The combined extract was dried over anhydrous magnesium sulfate. After the removal of the drying agent by suction/filtration, the filtrate was concentrated to about 30 ml and passed through a small chromatography column containing about 50 g of silica gel saturated with hexane. The column was then eluted with 1:1 methylene chloride/hexane. Upon removal of the solvent from the first fractions, the desired product was isolated as a yellow solid. Yield: 11.0 g (90%). Anal Calc. for $C_{15}H_{11}NO_3$; C, 71.13; H, 4.38; N, 5.53. Found: C, 70.67; H, 4.51; N, 5.52. IR(KBr pellet): $\nu(CO)$ at 1646 cm$^{-1}$ vs; $\nu(NO_2)$ at 1534 cm$^{-1}$ and 1350 cm$^{-1}$ vs. Proton NMR (CDCl$_3$, δ in ppm): 3.30 (singlet, alicyclic protons, 4H); 7.17–7.32, 7.57–7.89, 8.14–8.65 (multiplet, aromatic protons, 7H).

EXAMPLE 7

Preparation of 4-benzocyclobutenyl-3-aminophenyl ketone.

4-benzocyclobutenyl-3-nitrophenyl ketone (11.0 g, 43.4 mmol) was partially dissolved in a mixed solvent (30 ml of ethyl acetate and 70 ml of methanol in a 300 ml round-bottomed flask). To the suspension was added 0.95 g of 10% Pd/C followed by the addition of 13.0 g (206 mmol) of ammonium formate. The black reaction mixture was then stirred magnetically under an atmosphere of nitrogen at room temperature for about 3 hrs. The reaction mixture was then filtered through a bed of Celite and the solid residue was washed with methanol until the filtrate was colorless. The yellow-green filtrate was subsequently subjected to rotary evaporation. The resultant viscous amber liquid was mixed with about 50 ml of methylene chloride and the solution formed was washed with 2 portions (100 ml) of H$_2$O. Finally, the methylene chloride extract was dried over anhydrous magnesium sulfate. After the removal of the drying agent and the solvent, a very viscous and amber liquid was isolated. Despite drying in the vacuum (70° C.) for more than 24 hours, it never solidified. Yield: 8.0 g. It was used in the subsequent synthesis without further purification. Mass Spectroscopy: M$^+$, $m/e$=223, 100%. IR(KBr pellet). $\nu(NH_2)$ at 3365 vs and 3460s; $\nu(CO)$ at 1646 vs. Proton NMR (CDCl$_3$, δ in ppm): 3.21 (singlet, 4H, alicyclic protons); 3.83 (singlet, 2H, NH$_2$); 6.73–7.77 (multiplet, 7H, aromatic protons).

EXAMPLE 8

Preparation of 4-benzocyclobutenyl-3-(N-maleimido)phenyl ketone.

1.98 g (8.87 mmol) of 4-benzocyclobutenyl-3-aminophenyl ketone was dissolved in about 35 ml of dimethyl acetamide and the resultant solution was stirred at about 10° C. under nitrogen for about 20 minutes. Then, freshly purified maleic anhydride (0.87 g, 8.87 mmol) was added in one portion. The bright yellow solution was stirred at 10° C. for 30 minutes and then at room temperature for another 5 hours. A mixture of triethylamine (1.0 ml) and acetic anhydride (4.0 ml) was added to the reaction mixture, which turned dark slowly. After the reaction mixture had been stirred under nitrogen at room temperature overnight, it was poured into a 1-liter beaker containing about 600 ml of cold aqueous sodium chloride (30 g). The dark brown solid precipitate was collected on a fritted filter funnel and washed with a copious amount of water. After it had been air-dried (with suction) for about 2 hours, the dark brown crude solid was extracted with methylene chloride. The methylene chloride extract was dried over anhydrous magnesium sulfate. After the removal of the drying agent, the methylene chloride solution was concentrated and passed through a coarse fritted funnel containing a bed of SiO$_2$ (approximately 20 g). Methylene chloride was used as the eluent. The yellow filtrate collected was subjected to rotary evaporation. Dark amber oil was isolated and upon standing at room temperature for several days, it solidified. Yield: 1.66 g (62%). Anal. Calc. for $C_{19}H_{13}NO_3$: C, 75.24; H, 4.32; N, 4.62. Found: C, 74.70; H, 4.52; N, 4.58 . Mass Spectroscopy: M$^+$, $m/e$=303, 100%. Proton NMR (CDl$_3$, δ in ppm): 3.30 (singlet, 4H, alicyclic protons); 6.92 (singlet, 2H, olefinic protons); 7.14–7.27, 7.61–7.88 (multiplet, 7H, aromatic protons). IR (KBr pellet): $\nu$(alicyclic C—H) at 2928 W; $\nu$(maleimide) at 1750 VW and 1718 vs; $\nu$(keto-carbonyl) at 1653 ms.

EXAMPLE 9

Preparation of 3-(N-4-nitrophthalimid)phenyl-(4-benzocyclobutenyl) ketone.

4-benzocyclobutenyl-3-aminophenyl ketone (2.00 g, 8.96 mmol) was dissolved in about 50 ml of dimethyl acetamide. To the resultant yellow-orange solution was added 4-nitrophthalimide (1.73 g, 8.96 mmol). The dark amber reaction mixture was then stirred at room temperature under nitrogen for about 5 hours. After a mixture of acetic anhydride (4.0 ml) and pyridine (3 ml) had been delivered, the reaction mixture was stirred at room temperature under nitrogen overnight. The dark reaction mixture was poured into a 1-liter beaker containing about 600 ml of chilled aqueous sodium chloride (30 g) solution. The light yellow precipitates were collected on a fritted filter funnel and washed with a copious amount of water. It was then air-dried, with suction overnight. The dried crude product was extracted with methylene chloride. The resultant methylene chloride solution was dried over anhydrous magnesium sulfate. The methylene chloride solution was then concentrated to about 30-40 ml and hexane was then added slowly to precipitate out off-white solid product, which was subsequently collected on a fritted filter funnel, washed with hexane and air-dried overnight. Yield: 2.80 (71%). Anal. Calc. for $C_{23}H_{14}N_2O_5$: C, 69.32; H, 3.54; N, 7.03. Found: C, 68.23; H, 3.58; N, 6.82. Mass Spectroscopy: M$^+$, 398. 71.6%. Infra spectroscopy (KBr pellet): 1786 m and 1730 vs assignable to the asymmetric and symmetric stretches of the imide group; 1654 vs, assignable to the keto-carbonyl group; 15345 and 1345 s, assignable to the asymmetric and symmetric stretches of the nitro group.

EXAMPLE 10

Preparation of 3-(N-4-aminophthalimid)phenyl-(4-benzocyclobutenyl) ketone.

3-(N-4-nitrophthalimid)phenyl-(4-benzocyclobutenyl) ketone (2.18 g, 5.47 mmol) was dissolved in about 20 ml of ethyl acetate, followed by the addition of 0.1 g of palladium on carbon (10%) and about 30 ml of methanol. To the resultant black mixture was added ammonium formate (2.00 g, 31.7 mmol) in one portion. The reaction mixture was subsequently stirred under nitrogen for about 4 hrs, at which time the thin-layer chromatogram of the reaction mixture indicated all the starting nitro-compound had been consumed. Hence, the olive-green reaction mixture was filtered through a bed of Celite and the solid residues were extracted with ethyl acetate. The yellow-green filtrate was then subjected to rotary evaporation to afford yellow waxy solid, which was taken up in a mixture of methylene chloride and water. The methylene chloride layer was separated and dried over anhydrous magnesium sulfate. After the removal of the drying agent and the solvent, about 1.60 g of amber solid product was obtained and used in the subsequent synthesis without further treatment. IR(KBr pellet): $\nu(NH_2)$ at 3364 and 3222 cm$^{-1}$; $\nu$(aliphatic C-H) at 2970 and 2930 cm$^{-1}$; $\nu$(imide) at 1765 and 1714 cm$^{-1}$; $\nu$(keto-carbonyl) at 1652 cm$^{-1}$. Mass Spectroscopy: M$^+$, m/e=368, 100%.

EXAMPLE 11

Preparation of 3-(N-4-maleimido-phthalimid)phenyl-(4-benzocyclobutenyl) ketone.

The crude 3-(N-4-aminophthalimid)phenyl-(4-benzocyclobutenyl) ketone (1.50, ca. 4.07 mmol) was completely dissolved in about 80 ml of methylene chloride and maleic anhydride (0.40 g, 4.08 mmol) was added neat. The resultant reaction mixture was stirred under nitrogen overnight. It remained dark brown and homogeneous throughout the period. After methylene chloride had been removed by rotary evaporation, about 80 ml of acetone was added, followed by the addition of 0.1 g of nickel acetate tetrahydrate, and a mixture of triethylamine (0.5 ml) and acetic anhydride (2.5 ml). The reaction mixture was stirred at room temperature under nitrogen for another 17 hours. After the solvent had been removed via rotary evaporation, the residual dark oil was treated with about 50 ml of methylene chloride. The resultant solution was then poured into about 180 ml of H$_2$O in a separatory funnel. The methylene chloride layer was drained off and the aqueous phase was extracted with 2 portions (20 ml) of methylene chloride. The combined organic solution was dried over anhydrous magnesium sulfate. After the removal of the drying agent by filtration, the filtrate was concentrated and added to a small chromatographic column containing abut 50 g of SiO$_2$, saturated with hexane. The column was then eluted with 1:1 hexane/CH$_2$Cl$_2$. About 1.20 g of peach-colored solid was isolated from the first fractions. Yield: 67%. Anal. Calc. for C$_{27}$H$_{16}$N$_2$O$_5$: C, 72.31; H, 3.60; N, 6.25. Found: C, 71.97; H, 3.48; N, 6.10. Mass Spectroscopy: M$^+$, m/e=368, 100%. IR(KBr pellet): $\nu$(aromatic and olefinic C—H) at 3099 W; $\nu$(alicyclic C—H) at 2970 W and 2930 W; $\nu$(imide) at 1774 m and 1720 vs; $\nu$(keto-carbonyl) at 1653 ms. Proton NMR (CDCl$_3$, δ values in ppm): 3.27 (s, alicyclic protons); 6.98 (s, olefinic protons ); 7.16–7.26 (m, aromatic protons associated with benzocyclobutene moiety); 7.61–8.13 (m, aromatic protons associated with other aryl groups).

Having described the invention in detail and by reference to preferred embodiments thereof, it will be apparent that modifications and variations are possible without departing from the scope of the invention defined in the appended claims.

What is claimed is:

1. A compound of the formula

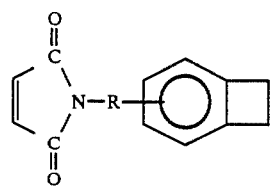

wherein R is a member selected from the group consisting of (a) (b) and (c), wherein (a) is

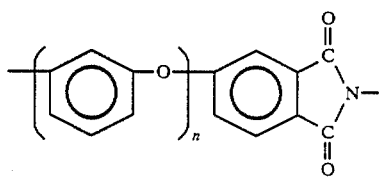

wherein n is 0 or 1;
(b) is

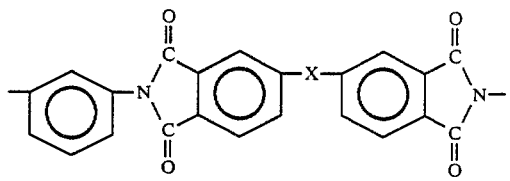

wherein X is a direct bond, —C(CF$_3$)$_2$—, —C(CH$_3$)$_2$—, —CH$_2$—, —O—, —S—, —CO—, —SO$_2$—, or

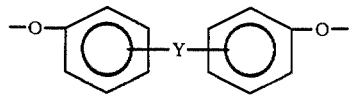

or

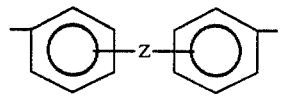

wherein Y is —C(CF$_3$)$_2$—, —C(CH$_3$)$_2$—, —O—, —S—, —CO—, or a direct bond, and Z is —C(CF$_3$)$_2$—, —C(CH$_3$)$_2$—, —CH$_2$—, —O—, —S—, —CO—, —SO$_2$—, or a direct bond; and wherein (c) is

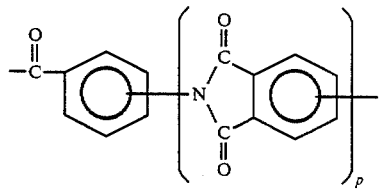

wherein p is 0 or 1.

2. The compound of claim 1 wherein R is represented by the formula

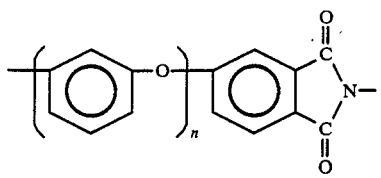

where n is 0 or 1.

3. The compound of claim 1 wherein R is represented by the formula.

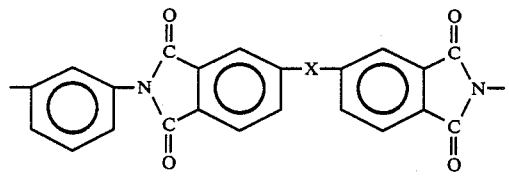

4. The compound of claim 3 wherein X is represented by the formula

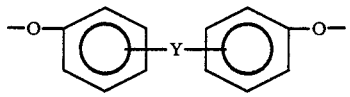

where Y is selected from the group consisting of —C(CF$_3$)$_2$—, —C(CH$_3$)$_2$—, —CH$_2$—, —O—, —S—, —CO—, —SO$_2$—and a direct bond.

5. The compound of claim 3 wherein X is represented by the formula

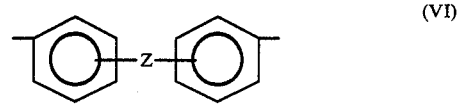

where Z is selected from the group consisting of —C(CF$_3$)$_2$—, —C(CH$_3$)$_2$—, —CH$_2$—, —O—, —S—, —CO—, —SO$_2$—and a direct bond.

6. The compound of claim 1 wherein n is O.

7. The compound of claim 1 wherein R is represented by the formula

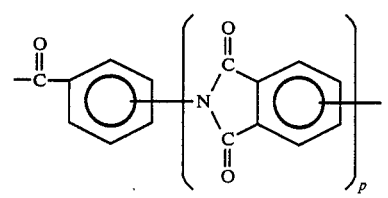

where p is 0 or 1.

* * * * *